United States Patent
Eck et al.

(10) Patent No.: US 10,588,870 B2
(45) Date of Patent: *Mar. 17, 2020

(54) CANNABINOID FORMULATIONS FOR INHALATION

(71) Applicant: EP Pharma, LLC, Fall River, MA (US)

(72) Inventors: Charles Raymond Eck, Shrewsbury, MA (US); Christopher L. Pelloni, Newtown, PA (US)

(73) Assignee: EP Pharma, LLC, Fall River, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,802

(22) Filed: Jul. 25, 2018

(65) Prior Publication Data

US 2018/0344634 A1 Dec. 6, 2018

Related U.S. Application Data

(63) Continuation-in-part of application No. 15/634,249, filed on Jun. 27, 2017, now Pat. No. 10,064,821,
(Continued)

(51) Int. Cl.
*A61K 31/05* (2006.01)
*A61K 9/00* (2006.01)
(Continued)

(52) U.S. Cl.
CPC ............ *A61K 31/05* (2013.01); *A61K 9/0007* (2013.01); *A61K 9/008* (2013.01); *A61K 9/0073* (2013.01);
(Continued)

(58) Field of Classification Search
None
See application file for complete search history.

(56) References Cited

U.S. PATENT DOCUMENTS 6,509,005 B1  1/2003  Peart et al.
6,713,048 B2  3/2004  Peart et al.
(Continued)

FOREIGN PATENT DOCUMENTS

WO   2000024362       5/2000
WO   2003006010 A1    1/2003
(Continued)

OTHER PUBLICATIONS

Burstein; The cannabinoid acids, analogs and endogenous counterparts; Biuoorganic & Medicinal Chemistry 22(2014) 2830-2843.
(Continued)

*Primary Examiner* — Aradhana Sasan
(74) *Attorney, Agent, or Firm* — Irving M. Fisherman

(57) ABSTRACT

A cannabinoid active agent containing formulation comprising the active agent, an HFA propellant, optionally a terpenoid, and optionally a co-solvent is disclosed. At least two cannabinoids, each of which is required to be present in amounts of at least 20% of the total cannabinoid content of formulation are required to be present. Also disclosed is an inhalation method of administration of the formulation without the use of heat greater than 40° C.

24 Claims, 1 Drawing Sheet

Related U.S. Application Data which is a continuation of application No. 15/196,315, filed on Jun. 29, 2016, now Pat. No. 9,717,683.

(51) Int. Cl.

| | | |
|---|---|---|
| *A61M 15/00* | (2006.01) | |
| *A61K 31/352* | (2006.01) | |
| *A61K 36/185* | (2006.01) | |
| *A61K 9/46* | (2006.01) | |
| *A61K 47/10* | (2017.01) | |
| *A61K 31/353* | (2006.01) | |
| *A61M 11/04* | (2006.01) | |

(52) U.S. Cl.
CPC .......... *A61K 31/352* (2013.01); *A61K 31/353* (2013.01); *A61K 36/185* (2013.01); *A61K 47/10* (2013.01); *A61M 15/009* (2013.01); *A61K 2236/00* (2013.01); *A61K 2300/00* (2013.01); *A61M 11/04* (2013.01)

(56) References Cited

U.S. PATENT DOCUMENTS

| | | | |
|---|---|---|---|
| 7,726,310 | B2 | 6/2010 | Andrus et al. |
| 7,968,594 | B2 | 6/2011 | Guy et al. |
| 8,211,946 | B2 | 7/2012 | Whittle |
| 8,337,908 | B2 | 12/2012 | Letzel |
| 8,481,091 | B2 | 7/2013 | Ross |
| 8,512,767 | B2 | 8/2013 | Ross |
| 8,673,368 | B2 | 4/2014 | Guy et al. |
| 8,771,760 | B2 | 7/2014 | Guy et al. |
| 9,044,390 | B1 | 6/2015 | Speier |
| 9,205,063 | B2 | 12/2015 | Guy et al. |
| 9,717,683 | B1 * | 8/2017 | Eck ................... A61K 9/008 |
| 9,730,911 | B2 | 8/2017 | Verzura et al. |
| 10,064,821 | B2 * | 9/2018 | Eck ................... A61K 9/008 |
| 2005/0061314 | A1 | 3/2005 | Davies |
| 2005/0079136 | A1 | 4/2005 | Woolfe et al. |
| 2005/0165088 | A1 | 7/2005 | Whittle |
| 2007/0072939 | A1 | 3/2007 | Kupper |
| 2008/0017191 | A1 | 1/2008 | Davies et al. |
| 2010/0317729 | A1 | 12/2010 | Guy et al. |
| 2015/0165030 | A1 | 6/2015 | Rossi |
| 2015/0203434 | A1 | 7/2015 | Flockhart |
| 2015/0231108 | A1 | 8/2015 | Hearn et al. |
| 2015/0297653 | A1 | 10/2015 | Speier |
| 2016/0151275 | A1 | 6/2016 | Shurtleff et al. |
| 2017/0209409 | A1 | 7/2017 | Hartman et al. |
| 2018/0360772 | A1 * | 12/2018 | Eck ................... A61K 9/008 |

FOREIGN PATENT DOCUMENTS

| | | |
|---|---|---|
| WO | 2004016277 A2 | 2/2004 |
| WO | 2009043395 A9 | 4/2009 |
| WO | 2015195711 A2 | 12/2015 |
| WO | 2015198071 A1 | 12/2015 |
| WO | 2015200049 A1 | 12/2015 |

OTHER PUBLICATIONS

Supplementary Search Report from Corresponding European Application No. 178290948.2 (8 pages).

Administrator, Pure Analytics Blog; Acidic versus Activated Cannabinoids—Tips on How to Choose the Therapy Regimen that is Right for You; May 9, 2012; 3 pages. http://pureanalytics.net/blog/2012/05/09/acidic-versus-activated-cannabinoids-tips-on-hpw-to-choose-the-therapy-regimen-that-is-right-for-you/.

Throckmorton; Cannabinol:Barriers to Research and Potential Medical Benefits; Jun. 24, 2015; (9 pages) http:/www.fda.gov/newsevents/testimony/ucm453989.htm.

Cannabinoid; https://en.wikipedia.org/wiki/Cannabinoid; Jul. 25, 2016; 15 pages.

Romano et al; Cannabis Oil: chemical evaluation of an upcoming cannabis-based medicine; Cannabinoids 2013; 1(1): 1-11.

Brenneisen; Chemistry and Analysis of Phytocannabinoids and Other Cannabis Constituents; Chapter 2 from Forensic Science and Medicine: Marijuana and the Cannabinoids, Edited by M.A.ElSohly (Humana Press Inc., Totowa, NJ 2007).

Scientists figure out how much pot is in a joint; http://www.newser.com/story/228246/scientists-determine-how-much-pot-is-in-a-joint.html; Jul. 18, 2016.

Public Information Report on Sativex Oromucosal Spray UK/H/961/01/DC; pp. 1-46; 2016; www.mhra.gov.uk/con 2033.

Whittle, et al; Prospects for New Cannabis-Based Prescription Medicines; Journal of Cannabis Therapeutics vol. 1, No. 3/4, 2001 pp. 183-205.

USP 39, Physical Tests, Section 601 Inhalation and Nasal Drug Products, pp. 423-449, official from May 1, 2016; The United States Pharmacopoeia.

Guidance for State Medical Cannabis Testing Programs; Association of Public Health Laboratories; May 2016 https://www.aphl.org/aboutAPHL/publications/Documents/EH-Guide-State-Med-Cannabis-052016.pdf.

Takeda, Shuso, et al;, Cannabidiolic Acid as a Selective Cyclooxygenase-2-Inhibitory Component in Cannabis; Drug Metabolism and Disposition, vol. 36, No. 9, 1917-1924, 2008.

Scott, Katerine Ann, et al; Enhancing the Activity of Cannabbidiol and other Cannabinoids In Vitro Through Modifications to Drug Combinations and Treatment Schedules; Anticancer Research, 33, 4373-4380 (2013).

Examination report No. 2 for standard patent application in Australian Patent Application 2017288899 dated Sep. 16, 2019.

* cited by examiner

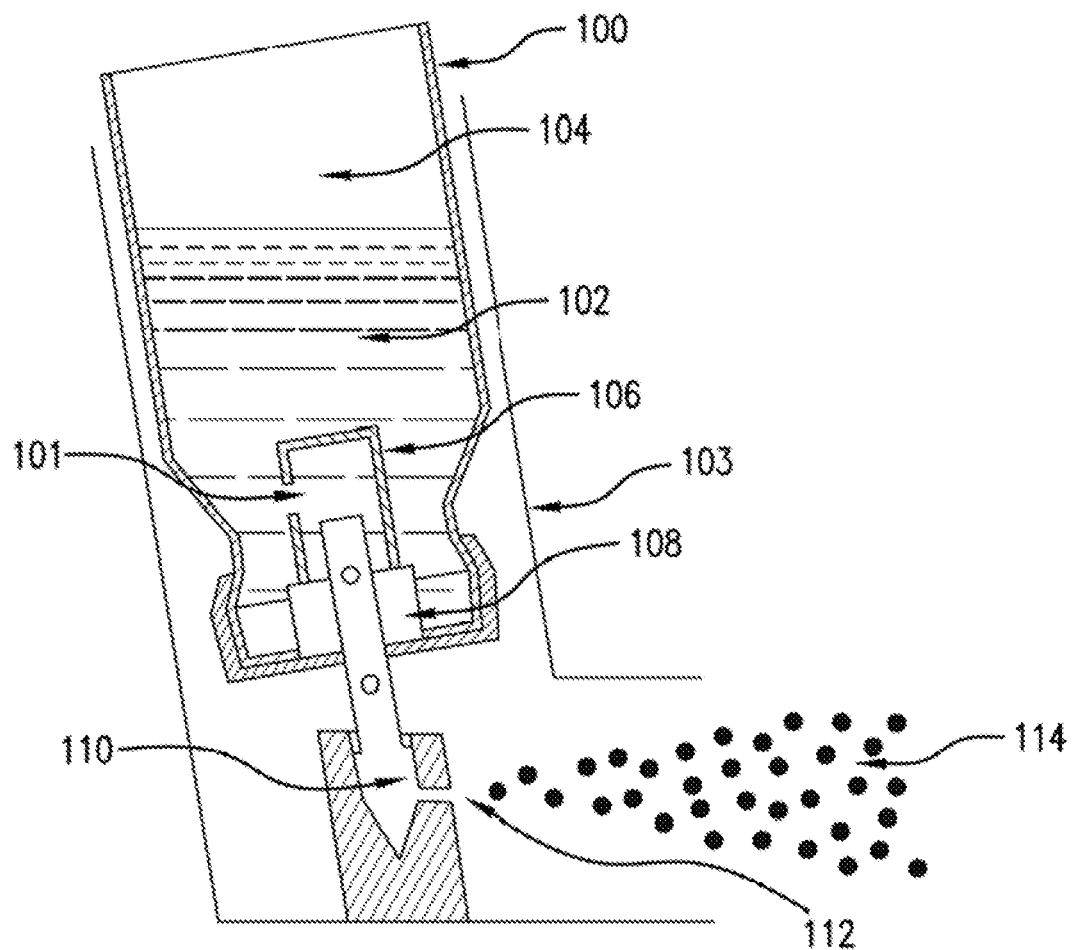

CANNABINOID FORMULATIONS FOR INHALATION

CROSS-REFERENCE TO RELATED APPLICATIONS

This application is a continuation-in-part of U.S. patent application Ser. No. 15/634,429, filed Jun. 27, 2017, which is a continuation of U.S. patent application Ser. No. 15/196,315, filed Jun. 29, 2016, now issued as U.S. Pat. No. 9,717,683 on Aug. 1, 2017; and this application is also a continuation-in-part of PCT/US2017/038483, filed Jun. 21, 2017, which claims priority of U.S. patent application Ser. No. 15/196,315.

STATEMENT REGARDING FEDERALLY SPONSORED RESEARCH OR DEVELOPMENT

Not Applicable

FIELD OF THE INVENTION

The present invention is directed to the field of cannabinoid active agents with or without additional terpenoid compounds. In preferred embodiments, the invention is directed to cannabinoid active agents that are substantially in the acid form thereof, especially to those selected from cannabidiolic acid (CBD Acid), tetrahydrocannabinolic acid (THC Acid), tetrahydrocannabivarinic acid (THCV Acid), cannabinolic acid (CBN Acid), and cannabigerolic acid; also with or without additional terpenoid compounds. The invention also relates to the field of formulations of these materials for inhalation therapy, as well as to the field of inhalation therapeutic therapies.

BACKGROUND OF THE INVENTION

The field of therapeutic use of cannabinoid active agents has blossomed in recent decades as the therapeutic use of cannabinoids has become legalized in more and more jurisdictions. Most uses of cannabinoids, whether as whole plant, extracts of the plants, and as purified compounds (natural or synthetic), has been primarily in the direction of (a) ingesting the materials orally either as solid oral dosage forms or by means of being baked into various orally ingestible baked goods, (b) delivery to the lungs by virtue of (1) smoking cannabinoid containing plant parts, or (2) vaporizing extracts (partially or highly purified compounds)—whether solid or liquid—via the application of heat in order to vaporize the cannabinoid containing substance. While these methods of administration do deliver active principles, each of these methods suffer from various defects and problems. Generally, the "Acid Form" of a cannabinoid differs from its "non-acid" counterpart in that the "Acid Form" has from 1 to 3 carboxylic acid groups (or esters, amides, or salts thereof) as part of its structure at positions where the non-Acid counterpart has no such groups present. (See the more detailed description with respect to Formulae I through IX below). For example, one problem is the fact that the application of heat to cannabinoids changes the composition of the cannabinoids in significant part from for example cannabinoid acids to corresponding non-acid cannabinoids, generally by reduction or cleaving of these carboxylic groups. In the case of THC (tetrahydrocannabinol), the structurally different acid version of the material (tetrahydrocannabinolic acid (THCA)) is substantially less psychotropic than the tetrahydrocannabinol itself. Thus, application of heat, in the course of delivery by smoking the material or in the use of vaporizers, increases the psychoactive effects. In the case of CBD (cannabidiol) and the acid forms of the other cannabinoids, which are not psychotropic, the structurally different acid version of the material (cannabidiolic acid (CBDA) et cetera) have shown increased in-vivo activity compared to the non-Acid form of cannabidiol itself and the corresponding non-Acid forms of the other cannabinoids, respectively. Thus, the application of heat in the course of smoking the material or in the use of vaporizers, modifies the in-vivo effects. As the therapeutic uses of cannabinoids are directed to activities other than the psychoactive effects, the use of smoking and vaporizing as delivery methods are disadvantageous. In addition, oral ingestion modes of administration, including sublingual administration, require significant doses in order to obtain the desired effects due to a very high first pass metabolism effect of cannabinoids. Thus, administration methods that can avoid the first pass metabolism effect would be desirable as allowing for reduction in dosage amounts needed to obtain desired effects.

OBJECTS OF THE INVENTION

It is among the objects of the present invention to provide a formulation of cannabinoid active principles that can avoid the first pass metabolism effects associated with oral delivery or ingestion (including sublingual delivery).

It is another object of the invention to provide a formulation of primary cannabinoid active agents that are each substantially in the "Acid-Form" thereof that can be administered in suitable doses without the use of heating above 40° C.

It is another object of the invention to provide a formulation of synthetic or semi-synthetic cannabinoids that are each substantially in the "Acid-Form" that can be administered in suitable doses without the use of heating above 40° C.

It is still another object of the invention to provide an inhalation suitable formulation (especially solution formulations) of one or more cannabinoid active principles which are substantially in the "Acid-Form" thereof.

It is still another object of the invention to provide an inhalation suitable formulation of one or more cannabinoid "Acid-Form" active principles capable of being delivered to a subject in microdoses, especially metered doses of from less than 10 ug to 20 mg per dose.

Still a further object of the invention is to provide an inhalation suitable formulation of one or more "Acid-Form" cannabinoid active agents where such formulation has as a principle solvent, a pharmaceutically acceptable propellant, with or without a pharmaceutically and inhalation suitable co-solvent.

An even further object of the invention is to provide a metered dose inhalation suitable formulation containing one or more cannabinoid "Acid-Form" active agents.

Yet an even further object of the invention is to provide a metered dose inhaler system for delivery of the foregoing cannabinoid "Acid-Form" containing formulations of the previous object of the invention.

Still an even further object of the invention is to provide a method of treatment of a cannabinoid Acid-Form active agent responsive condition via administration of an inhalation suitable formulation of the cannabinoid "Acid-Form" active agent without the use of the application of heat over 40° C. and without the use of burning.

Yet another object of the invention is to provide a metered dose inhaler that delivers one or more formulations of the previous objects of the invention in therapeutically effective amounts for one or more of the various cannabinoid "Acid-Form" responsive conditions, which therapeutically effective amount is substantially reduced relative to the dose needed for oral or sublingual administration thereof for the same condition.

Still another object of the invention is to provide a method of treatment of a cannabinoid responsive condition with substantially reduced psychoactive effects relative to administration by smoking or by vaporizing and at a substantially reduced therapeutically active dosage as compared to oral administration, sublingual administration, or topical administrations using a cannabinoid containing formulation wherein the primary cannabinoid compounds are each substantially in the "Acid-Form".

An even further object of the invention is a formulation in which substantially all cannabinoids present in the formulation are substantially in the "Acid-Form".

Still an even further object of the invention is a formulation in which all of the cannabinoids present in the formulation are substantially in the Acid-Form.

Yet an even further object of the invention is a formulation in which substantially all of the cannabinoids present in the formulation are in the "Acid-Form".

Yet an even further object of the invention is a formulation in which all of the cannabinoids present are all in the Acid-Form.

An even further object of the invention is a formulation as set forth in the foregoing objects which further contains at least one terpenoid in an amount in excess of that which is potentially naturally present in the formulation depending upon the source of the cannabinoid being incorporated into the formulation.

Still other objects of the invention will be recognized by those of ordinary skill in the art.

BRIEF SUMMARY OF THE INVENTION

These and other objects of the invention are surprisingly achieved by a formulation of (1) at least one cannabinoid active agent selected from the group consisting of a natural or synthetic cannabinoid active agent or mixtures thereof as an extract, in partially or completely purified form, or as a synthetic compound in partially or completely purified form, or a combination thereof, each of which cannabinoid is substantially in the Acid-Form thereof; (2) optionally one or more terpenoids; (3) dissolved in one or more pharmaceutically and inhalation acceptable propellant(s); (4) optionally in the presence of one or more pharmaceutically and inhalation acceptable co-solvent(s) for the cannabinoid active agents; which formulation is delivered via a metered dose inhaler device without the need for heating over 40° C. during delivery.

BRIEF DESCRIPTION OF THE DRAWING

FIG. 1 is a partial cross-sectional view of a metered dose inhaler generally known in the art.

DETAILED DESCRIPTION OF THE INVENTION

The present invention is a formulation of (1) a cannabinoid material selected from the group consisting of (a) a natural cannabinoid active agent in partially or completely purified form (which may include an extract), (b) a synthetic cannabinoid active agent in partially or completely purified form, and (c) mixtures thereof; dissolved in one or more pharmaceutically and inhalation acceptable propellant(s), optionally in the presence of one or more pharmaceutically and inhalation acceptable co-solvent(s) for the cannabinoid active agents; which formulation is delivered via a metered dose inhaler device without the need for heating over 40° C. during delivery and which has optionally one or more terpenoid compounds.

For purposes of this specification Major Cannabinoid active agents are each present in at least 20% of the total cannabinoids of the formulation, with the calculation of the percentage for Major or Non-Major being the combined amounts of the Acid-Form and Non-Acid-Form of a particular cannabinoid relative to all cannabinoids that are present, whether in Acid-Form or Non-Acid-Form. The Major cannabinoids are substantially in the Acid-Form, with substantially being at least 90%, preferably at least 95%, more preferably at least 98%, yet more preferably at least 99%, and most preferably completely in the Acid-Form thereof, with the balance of the Major Cannabinoid being in the corresponding Non-Acid-Form. Minor cannabinoids (those that are present between Acid-Form and Non-Acid-Form in amounts of less than 20% of the total cannabinoid content of the formulation), may be present in any blend of Acid-Form and Non-Acid-Form, but are preferably also substantially in the Acid-Form, with substantially being defined in the same manner as for the Major Cannabinoids. More specifically, the cannabinoid compounds of the invention are defined to include without limitation, those having any one of the structures I-IX below:

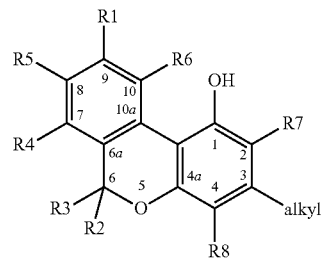

Formula I

Tetrahydrocannabinol-type
and
Cannabinol-type

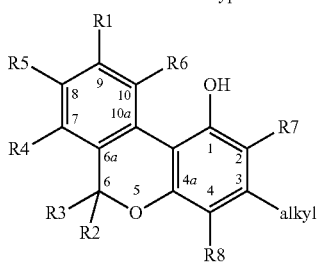

-continued
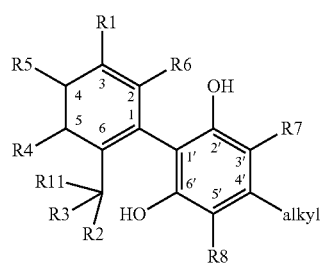
Cannabidiol-type
Formula II
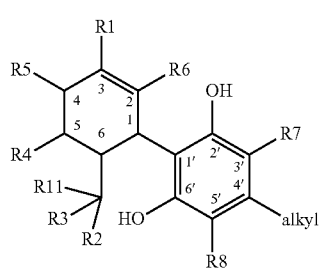
Formula IIa
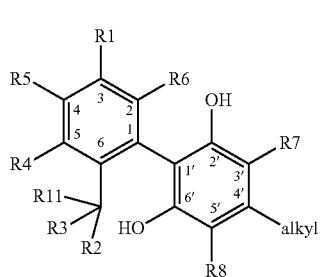
Formula IIb
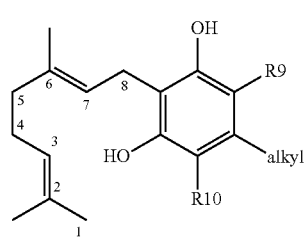
Cannabichromene-type
Formula III
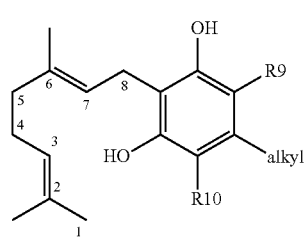
Cannabigerol-type
Formula IV
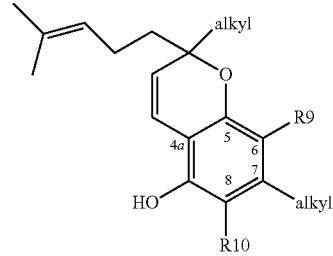
Cannabichromene-type
Alternate Formula III
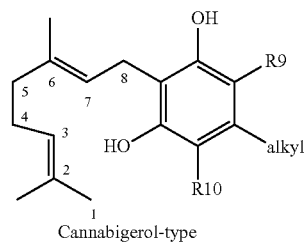
Cannabigerol-type
Formula IV
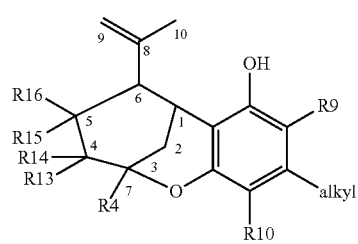
iso-Tetrahydrocannabinol-type
Formula V
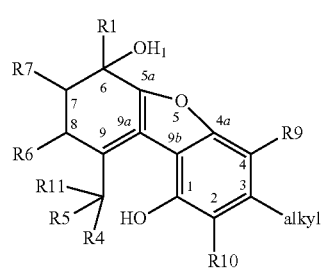
Cannabielsoin-type
Formula VI
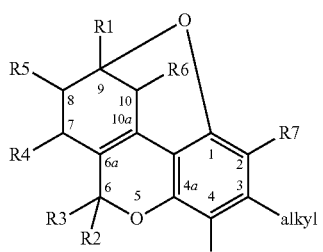
Cannabicitran-type
Formula VII Formula VIII

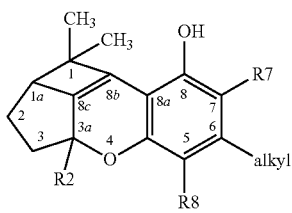

Cannabicyclol-type

Formula IX

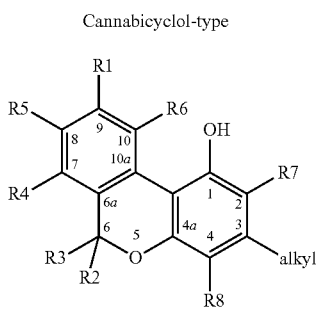

Cannabivarin-type wherein R1 is lower alkyl, —CH$_2$(OH), —CH(OH) lower alkyl, —CHO, —C(=O) lower alkyl, or —COOH or an ester or amide or salt of —COOH or an ester or salt of the alcoholic OHs, the complementary groups forming the esters and amides being pharmaceutically acceptable and preferably being lower alkyl (for esters with acidic functions in the structures shown) and mono-di- and tri-lower alkylamines (for amides with acidic functions in the structures shown) and lower alkylcarbonyl (for hydroxy functions in the structures shown);
R2 and R3 are independently H, lower alkyl, or together are =CH$_2$, or =CH-lower alkyl, or =C-(lower alkyl)(lower alkyl);
R4 is H or lower alkyl;
R5 and R6 are independently H or lower alkyl;
and further with respect to Structural Formula VI that R4 and R5 may also together form CH$_2$=;
R7-R10 are independently H, lower alkyl, —CH$_2$OH, —CHO, —COOH, or an ester or amide or salt thereof, the group completing the ester or amide or salt being independently selected from the same moieties as described above;
R11-R16 independently being H, or lower alkyl;
all recitations of "alkyl" without specific carbon length or modified by "lower" being C1-C10 in length; and all recitations of "alkyl" and "lower alkyl" being understood as being straight chain or branched chain. When such compounds of Formulae I-IX are Major cannabinoids, then at least R7 and R9 are substantially in the form of —COOH, or a pharmaceutically acceptable ester, pharmaceutically acceptable amide, or pharmaceutically acceptable salt thereof, where "substantially" is defined as above for Major Cannabinoids. When such compounds are Non-Major Cannabinoids, the full range of R groups in Formulae I-IX may be selected, but preferably R7 and R9 for these are also substantially in the "Acid-Form" as described above for the Major Cannabinoids. "Cannabinoid" compounds as used herein further includes each of the specifically named cannabinoids that are recited above or below. "Pharmaceutically acceptable salts" of a carboxy function in the above formulae I-IX include the lithium, potassium, sodium, calcium, magnesium salts and mixtures thereof. Preferably, the pharmaceutically acceptable salts of the carboxy function are selected from lithium, potassium, and sodium salts, most preferably, the sodium salt. "Pharmaceutically acceptable esters of the carboxy" function in formulae I-IX above include esters with ethanol, propanol, isopropanol, t-butanol, and glycerol, preferably esters with ethanol. Esters of free hydroxyl groups in the formulae I-IX may be selected from the group consisting of succinic acid, hemisuccininic acid, fumaric acid, malic acid, maleic acid.

The cannabinoid active agent is selected from any of the known cannabinoids. These include, without limitation, tetrahydrocanabinols (including without limitation Δ9 tetrahydrocannabinol and its isomers, especially, including without limitation, trans (−)-Δ9 tetrahydrocannabinol, and trans (+)-Δ9 tetrahydrocannabinol) and their isomers, tetrahydrocannabinolic acids (including without limitation Δ9 tetrahydrocannabinolic acid, and its isomers, especially, including without limitation, trans (−)-Δ9 tetrahydrocannabinolic acid, and trans (+)-Δ9 tetrahydrocannabinolic acid and their isomers) cannabidiol, cannabidiolic acid, cannabigerolic acid, cannabigerol, cannabigerovarinic acid, cannabigerolovarin, cannabichromenic acid, cannabichromene, cannabidivarin, cannabidivarinic acid, cannabivarin, cannabivarinic acid, tetrahydrocannabivarinic acid, tetrahydrocannabivarin, cannabinolic acid, cannabinol, cannabinodiol, cannabielsoin, cannabicyclol, and cannabicitran and isomers thereof, and various mixtures thereof. The foregoing cannabinoids further include the corresponding acid variations of any of the specifically mentioned non-acid variants. Preferably the Major Cannabinoids (each present in amounts in excess of 20% of the total cannabinoids of the formulation, where in the calculation to determine if, in a particular formulation, a cannabinoid is a Major or Minor cannabinoid, the corresponding Acid-Forms and Non-Acid-Forms are taken into account, and if a particular cannabinoid is a Major Cannabinoid for a particular formulation, (such Major Cannabinoid must be substantially in the Acid-Form) are selected from one or more of the compounds with formulae I-IX and of Δ9 tetrahydrocannabinol, Δ9 tetrahydrocannabinolic acid, cannabidiol, cannabidiol acid, cannabichromic acid, cannabichromene, cannabigerolic acid, cannabidivarin, cannabivarinic acid, tetrahydrocannabivarinic acid, tetrahydrocannabivarin, and cannabigerol, with the limitation that each Major Cannabinoid be substantially in the Acid-Form. Preferable the Minor Cannabinoids are selected from the same group, but they do not need to be substantially in the Acid-Form, but preferably are in the Acid-Form. Even more preferably, the cannabinoid material is one or two cannabinoid pairs (Acid Form/Non-Acid Form) selected from tetrahydrocannabinol (preferably a Δ9 tetrahydrocannabinol)/tetrahydrocannabinolic acid (preferably a Δ9 tetrahydrocannabinolic acid) and cannabidiol/cannabidiolic acid, which may have "very small amounts" of additional cannabinoids as well, the "very small amounts" being a weight/weight % of not greater than 20% (more preferably not greater than 10%, still more preferably not greater than 5%) relative to the total cannabinoid content of the formulation. The total Major Cannabinoid active agents are present in an amount of at least 80% of the total formulation cannabinoid content on a wt/wt basis. In still other embodiments, the Major Cannabinoids are combinations of at least two Major Cannabinoids, more preferably a mixture of either CBD Acid and/or THC Acid with at least one other Major Cannabinoid which is neither of CBD Acid and/or THC Acid. Unless, "cannabinoid acid" is specifically being distinguished from "non-acid cannabinoid" in this specification, the term "cannabinoid" without the qualifier "acid" is deemed to include both the cannabinoid acid forms and the cannabinoid non acid forms collectively.

The cannabinoids, regardless of their source or whether an extract, a partially purified cannabinoid, or a highly purified cannabinoid, or mixtures thereof, can be dissolved in either the pharmaceutically acceptable, inhalation acceptable propellant alone or first dissolved in a small amount of pharmaceutically acceptable, inhalation acceptable co-solvent. Where concentrations above the solubility of the cannabinoid components in the propellant are desired, the co-solvent can be added to obtain higher concentrations of these materials without the use of heat above the temperatures indicated elsewhere in this specification and in any event without the use of heating the material beyond 40° C. or more preferably without heating the material beyond the more preferred temperatures specified below in this paragraph. The pharmaceutically acceptable, inhalation acceptable co-solvent is selected from, without limitation, ethanol, propanol, propylene glycol, glycerol, polyethylene glycol (preferably without limitation PEG 300 or PEG 400), or mixtures thereof, preferably selected from ethanol, propanol, propylene glycol, and glycerol, more preferably ethanol. When used, the co-solvent is present in an amount of from about 0.05% by wt, up to 30% by wt based on the total of the propellant and co-solvent, more preferably, the co-solvent is present in ranges having a lower limit selected from 0.05%, 0.06%, 0.07%, 0.08%, 0.09%, 0.1%, 0.15%, 0.2%, 0.25%, 0.30%, 0.35%, 0.40% 0.45%, 0.5%, 0.55%, 0.6%, 0.65%, 0.70%, 0.75%, 0.8%, 0.85%, 0.9%, 0.95%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.25%, 3.5%, 3.75%, 4.0%, 4.25%, 4.5%, and 5.0% by wt; and an upper limit selected from 0.5%, 0.55%, 0.6%, 0.65%, 0.70%, 075%, 0.8%, 0.85%, 0.9%, 0.95%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2/5%, 2.6%, 2.7%, 2.8%, 2.9%, 3.0%, 3.25%, 3.5%, 3.75%, 4.0%, 4.25%, 4.5%, 4.75%, 5.0%, 10%, 15%, 20%, 25%, and 30% by wt provided that the particular upper limit selected is greater than the particular lower limit selected, each range being the amount of co-solvent relative to the combination of co-solvent and propellant, each % being weight/weight %. In addition to being a co-solvent, the co-solvent may be suitably used as a process aid to remove various insoluble contaminants (which may be present with the cannabinoid) before adding the pharmaceutically acceptable, inhalation acceptable propellant. In such situation, the cannabinoid material can be dissolved in the co-solvent, and the solution filtered to remove any non-solubilized components and the filtered solution is then utilized. The filtration procedure can occur at room temperature or after cooling of the ethanol (or other co-solvent) solution. If desired, mild heating can be used in the dissolution process, but is not to exceed a temperature selected from 40° C., 35° C., and 30° C., preferably without raising the temperature above a temperature selected from 35° C., and 30° C., most preferably without the application of heat at all. (If it is desired to remove the particular co-solvent above after the filtration, such removal can be done under the same conditions set forth below for the solvents that are not inhalation compatible.) Alternatively, if it is desired, for insoluble material removal, to use a solvent that is not acceptable for inhalation or is not compatible with the propellant, such solvent may be used to dissolve the cannabinoids, filter out any non-solubles, and then remove the inhalation unacceptable solvent without the application of heat that would cause conversion of any of the present cannabinoids Acid-Forms into cannabinoid Non-Acid-Forms. Thus, vacuum evaporation without any heating or without raising the temperature above a temperature selected from 40° C., 35° C., or 30° C., preferably without raising the temperature above a temperature selected from 35° C., or 30° C., most preferably without the application of heat at all can be used. Suitable solvents that are not both inhalation acceptable and non-interactive with the propellant for this "purification" aspect are limited to those that can be removed suitably under these conditions. Such solvents that are either or both not inhalation acceptable and/or are incompatible with the propellant and suitable as per the above limitations include, but are not limited to, butane, pentane, hexanes, heptanes, diethyl ether, ethyl acetate, methylene chloride, chloroform, acetone, methanol and mixtures thereof is particularly preferred. Where mixtures of solvents are desired to be used for the removal of the insolubles, such mixtures can be of the "co-solvents", mixtures of the "non-co-solvent solvents" or mixtures of both, provided that if any non-cosolvent solvent is used, at least all of the non-co-solvent solvents must be removed before further formulation.

Cannabinoid extracts frequently have as part of the extract, certain terpenoids in small concentrations relative to the total extract. The present invention further includes optionally adding one or more terpenoids set forth below in amounts such that the total terpenoid content is in excess of that present in the cannabinoid material being utilized as a source for the cannabinoids in the present invention. In other words, if an extract already having some terpenoids present is being used for the instant formulation, further addition of any amount of additional terpenoid brings the total terpenoid content to beyond that which is naturally present. When highly purified cannabinoids are used, their natural terpenoid content is extremely low and further addition of virtually any amount of additional terpenoid brings the total terpenoid amount to beyond that naturally present. Synthetic cannabinoids do not have terpenoids naturally present and therefore, any addition of terpenoid is acceptable. The terpenoids for use in the present invention are preferably selected from the group consisting of camphene, camphor, carene, caryophyllene, geraniol, humulene, limonene, linalool, menthol, myrcene, phellandrene, pinene, pulegone, sativene, terpineol, terpinolene, and mixtures thereof; preferably selected from the group consisting of menthol, limonene, terpineol, and mixtures thereof; most preferably menthol. When the terpenoids are used, they are present in a total amount of terpenoid in the range of from 0.005% w/w of the formulation to 0.1% w/w of the formulation; preferably in a total w/w amount relative to total formulation of a range selected from those having a lower range end point of 0.005%, 0.006%, 0.007%, 0.008%, 0.009%, 0.01%, 0.02%, 0.03%, 0.04%, 0.05%, 0.06% and an upper range end point selected from 0.03%, 0.04%, 0.05%, 0.06%, 0.07%, 0.08%, 0.09%, and 0.1%, provided that the lower range end point selected is less than the upper range end point being selected.

Propellants for the present invention are the pharmaceutically acceptable, inhalation acceptable hydrofluoroalkanes (HFAs). These include, but are not limited to, HFA 134a (tetrafluoroethane) HFA 227 (heptafluoropropane) and mixtures thereof; HFA 134a and HFA 227 being readily available in the marketplace from Mexichem Fluor, Inc. The propellants comprise the bulk of the present formulations, typically in the range of from 50% wt/wt to 99.5% wt/wt, preferably in the range from 60% to 99%, more preferably in the range 80 to 99% and most preferably in the range of 90% wt/wt to 99% wt/wt. Usually, the formulation comprises the active materials, the propellant and optionally the co-solvent, preferably consists essentially of the active materials, the propellant and optionally the co-solvent, still more preferably the formulation consists of the active materials, the propellant and optionally the co-solvent.

For example, in the case of a 100 ul metered dose inhaler valve, the delivered dose amount (from the metered dose inhaler unit) of cannabinoid material present in the formulation is from 0.01 mg to 20 mg per 100 ul actuation of formulation (where the shot weight of the emitted volume (100 ul) of formulation would range from 80 mg to 140 mg depending upon the presence of (and the particular) co-solvent and the particular HFA used at 20° C. (for example using 100% HFA 227 and active agent, the shot weight of 100 ul of formulation is about 140 mg); preferably in a range, per 100 ul of formulation, selected from those having a lower limit selected from 0.01 mg, 0.02 mg, 0.025 mg, 0.03 mg, 0.04 mg, 0.05 mg, 0.06 mg, 0.07 mg, 0.075 mg, 0.08 mg, 0.09 mg, 0.1 mg, 0.25 mg, 0.5 mg, 1 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.54 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.25 mg, 4.5 mg, 4.75 mg, and 5.0 mg, and an upper limit selected from 1.0 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.25 mg, 4.5 mg, 4.75 mg, 5.0 mg, 10 mg, 15 mg, and 20 mg provided that the selected upper limit is greater than the selected lower limit. A highly preferred concentration of the cannabinoid active agents in the formulation are selected from those above having a lower limit of at least 0.1 mg/100 ul of formulation and an upper limit of not more than 10 mg/100 ul of formulation based on the total Major Cannabinoid content. Actual dosage is a function of the concentration of the actives in the formulation and the volume emitted by the device and the respirable fraction. Appropriate adjustments in the size (volume of formulation emitted) of the valve, concentration of active material in the formulation, and respirable fraction (which can be varied with (a) the diameter of the stem block nozzle opening in the metered dose inhaler, (b) the amount and nature of co-solvent in the formulation, (c) the valve metering volume, all of which are well within the abilities of those of ordinary skill in the art having benefit of the present specification). For example, if the respirable fraction for a particular formulation is too low (i.e., dosage reaching the lungs is not sufficient), it can be increased by making the actuator orifice diameter opening smaller or reducing the co-solvent concentration (if possible), or adjusting the valve size to a smaller metering volume. If the respirable fraction is too high, one can adjust these same parameters in the opposite direction. Since these adjustments interplay with and affect one another, it is typical to construct a suitable device, test it for consistency between manufacturing lots, determine the dose delivered by the device, and determine the particle size of the emergent droplets and the estimated fraction of the dose reaching the lungs using in vitro methods. Thereafter, one adjusts one or more of the device or formulation parameters as mentioned above and re-determines the in-vitro respirable dose being delivered to the lungs with the modified formulation/device. The process is repeated as needed until such time as the precise formulation concentration, and device parameters are such that an appropriate actual dose (or suitable surrogate therefor) is determined. Such testing as set forth herein, while not insignificant, is not undue experimentation, is well within the abilities of those of ordinary skill in the art having benefit of the present specification, and is generally required by regulatory agency approval of the pharmaceutical product which includes both the metered dose inhaler package (canister, valve and actuator) and the formulation delivered thereby.

Non-limiting, typical properties of cannabinoids known in the art and include, without limitation, antibiotic, antifiungal, antiinflammatory, analgesic, anxiolytic, antipsychotic, antioxidant, antispasmodic, antiemtic, sedative, anorectic, antidiabetic, antidepressant, antiepileptic, antiinsomnia, antiischemic, antiproliferative, antiosioratic, antipsychotic, anxiolitic, appetite stimulant, bone stimulant, anti-cancer, and the formulations of the present invention may be used to treat one or more thereof. Suitable dosings emitted from the inhaler used in the formulation having CBD Acid (substantially in the Acid-Form) based formulations to deliver adequate therapeutic amounts would require a delivery of about 0.02 to 20 mg of active principles about every 8 to 12 hours, which is conveniently obtained by a metered dose inhaler delivering about 0.01 to 5 mg of active principles/spray with about 2-4 sprays per dose every 8-12 hours provided the dose of active is suitably and efficiently (30% or more respirable fraction as determined by Cascade Impaction) delivered into the lungs. In other words, a total daily dose of the active principles would be (0.02 to 20 mg per dosing)×(2-3 times a day)×(30% respirable fraction or more)=0.012 mg/day (based on a 30% respirable fraction and twice daily dosing) at the low end to 18 mg/day (based on a 30% respirable fraction and three times a day dosing) at the higher end; 0.02 mg/day (based on a 50% respirable fraction and twice daily dosing) at the low end to 30 mg/day (based on a 50% respirable fraction and three times a day dosing) at the high end, daily doses at a theoretical 100% respirable fractions being 0.04 mg/day to 60 mg/day.

Metered Dose inhalers of various design are generally available on the market. However, not all available metered dose inhalers suitably deliver the active substantially to the lungs, with a substantial portion being lost to the oral mucosa, throat, and the tongue. In situations where the first pass metabolism is not great, such a result may not play a significant role. However, in the present invention, substantial losses to the oral mucosa, throat, and tongue will substantially affect the results achieved. Thus, it may be necessary to conduct a certain degree of experimentation with existing metered dose inhaler components or construct modifications thereof based on the results of such experimentation so as to meet target specific demands. The components referred to are the formulation (as described above), the container, the metering valve, and the actuator device. A typical metered dose inhaler of the art is shown in FIG. 1. FIG. 1 illustrates a canister/valve/actuator combo 100 used to contain and aerosolize a liquid formulation 102 of the present disclosure. The canister/valve combo 100 is received within a stem block cavity in an actuator 103, or inhaler. The liquid formulation 102 substantially fills a retaining cup 106 positioned in the valve of the canister 100. A propellant 104 is used in the formulation by forming liquified propellant, a major part of the liquid formulation 102. When the canister 100 is pushed downward within the actuator 103, a metering chamber 108, in the valve which contains a spring releases a precise, predetermined metered amount of the liquid formulation 102. The released liquid formulation 102 enters the expansion chamber 110 where the liquid formulation 102 is released and expands. The formulation 102 then exits an actuator mouthpiece 112 forming an aerosolizing formulation 114. The aerosolized formulation 114 is formed of droplets or particles measuring between one (1) and five (5) micrometers in diameter, for example, 2 micrometers to 3 micrometers in diameter.

In use, a user places their mouth over the exit of the actuator 103, press the canister 100 downward against the valve/actuator 103 and inhale deeply to carry the aerosolized formulation cloud 114 into the alveoli of the deep lungs, where active ingredients in the aerosolized formulation 114 are deposited or absorbed rapidly into the blood stream, resulting in a faster perceived benefit of effect of the active ingredient while simultaneously bypassing first pass liver and stomach metabolism associated with oral drug delivery.

The pharmaceutical solution formulations in hydrofluoroalkanes (HFAs) used in the present invention are filled into canisters suitable for delivering pharmaceutical aerosol formulations. Canisters for use in metered dose inhalers in the present invention generally comprise containers capable of withstanding the vapor pressure of the HFA propellant, such as plastic, or plastic coated glass bottles or preferably a metal can, for example a stainless steel or aluminum can which is preferably anodized, organic and/or plastic coated. Generally suitable materials can be found in the disclosures of WO/2015/195711, and WO/2015/200049, both of which are incorporated by reference with respect to suitable materials for metered dose inhaler components. In the event of a formulation incompatibility with a particular container, one of the alternative containers above should be tried, preferably plastic coated containers or anodized aluminum, stainless steel or glass. The container is sealed with a metering valve, the metering valve comprising a metering chamber is designed to deliver a metered amount of the formulation per actuation and incorporates a gasket to prevent leakage of propellant through the valve. The gasket may comprise any suitable elastomeric material such as for example low density polyethylene, chlorobutyl, black and white butadiene acrylonitrile rubbers, butyl rubber, and neoprene. A valve stem extends from the metering valve and acts as a conduit to pass the metered dose into a nozzle block situated in the actuator body in which the valve stem is inserted Suitable valves are commercially available from manufacturers well known to the industry.

Each filled canister is fitted into a suitable channeled device (actuator) prior to use to form a metered dose inhaler package for administration of the medicament into the lungs or nasal cavity, preferably into the lungs, of a patient. In a typical arrangement, the valve stem is seated into a nozzle stem block which comprises an actuator orifice leading then to an expansion chamber/mouthpiece. This expansion chamber/mouthpiece is how the patient interacts with the inhaler device to inhale the dose emitted upon actuation of the device. Conventional HFA actuators have variable actuator orifice diameters ranging from 0.1 to 0.6 mm. The choice of actuator orifice size is decided primarily by the formulation ingredients, the physical properties of the formulation and the lung or nasal target areas. The goal of this choice is to deliver highly respirable doses (at least 30%, preferably at least 35%, more preferable at least 40%, still more preferable, at least 45%, most preferably at least 50%) capable of reaching the lung (without significant losses to the actuator, valve, canister, the oral cavity, and by exhalation).

This selection effort requires significant testing of the delivery characteristics of the chosen package (actuator, valve, canister) with the specific test formulation. While not all of these tests are relevant for the determination of a suitable metered dose inhaler, many of the tests for product uniformity and reliability of the respirable fraction set forth in the United States Pharmacopeia (USP) 39, official from May 1, 2016, Physical Tests (601) Inhalation and Nasal Products, p. 423-449 Chapter on Physical Tests and Determinations (incorporated herein by reference), are useful for the determination of whether a particular formulation in conjunction with a particular metered dose inhaler will meet the limitations of the present invention. Once tested to obtain the particular results of a particular formulation used with a particular metered dose inhaler, those of ordinary skill in the art will be able to adjust active agent concentration, the concentration or presence of any co-solvent, actuator design, and jet orifice diameter in order to achieve the appropriate combination of concentration, volume of delivery of formulation per actuation, and respirable fraction so as to achieve the desired dosages as set forth herein. Where a single actuation is insufficient to deliver the full dose target, multiple actuations can be used at a particular dosing point in order to achieve a suitable total dose.

As stated above, the overall objective of the present invention is to achieve a therapeutically effective amount of active agent(s) to the lung with a minimal amount of losses to the oral cavity and metered dose inhaler components. This allows for the elimination of excessively large doses that might otherwise be needed in order to achieve the desired therapeutically effective amount where losses to the oral cavity are significant (which may give rise to undesirable side effects). It should be noted that the following tests are not limitations on the invention but are merely a convenience for testing product to determine whether particular devices and formulations when used in combination will result in a method, combination (device with the formulation), or treatment within the scope of one or more claims of the present invention.

Where the various in vitro tests are detailed in the USP (USP 39, chapter 601), those tests and testing equipment is the preferred method of testing. It is recognized that the USP allows for a number of variations in the testing, but since the ultimate key result is a respirable fraction (for example at least 30%) of a particular amount of active agent reproducibly delivered by the metered dose inhaler utilizing a particular formulation is what is important, the precise manner of obtaining these values is described in a validated test method developed for the specific product. The important aspect is that one knows how much of the active agent mass is delivered out of the metered dose inhaler per actuation and what fraction of that amount is delivered in a manner that is deposited in the lungs of a user. Some tests specified by the USP are for testing of product uniformity, metered dose inhaler to metered dose inhaler, some are for testing metered dose inhaler consistency of delivered amount per actuation. These are performed to assure that the reliability of the metered dose inhaler unit used is properly working so that the remaining test results can be relied upon. Other tests are directed to determination of the respirable dose itself, which is important to the value of the present invention in reducing the amount of cannabinoid active agent needed to be used per target dose to obtain a specific treatment effective amount.

The various tests one of ordinary skill in the art may use that are in the USP or that are in addition to those in the USP, or that are alternatives to those in the USP but only after a correlation between the USP test and the alternative has been appropriately validated include, but are not limited to:

1. Spray actuation content uniformity throughout the life of the unit (beginning, middle and end stages of use) (testing reliability of the metered dose inhaler unit being used). This test is detailed in USP 39, chapter 601 and should be conducted in accordance therewith.

2. Fine particle dose and fine particle fraction (respirable fraction) thru the life of the unit by Cascade impaction technologies (determination of the respirable fraction). This test is detailed in USP 39, chapter 601 and should be conducted in accordance therewith. At such time as a product of the present invention is available on the market, samples of such product should be tested in any specific protocol as a confirmation that the specific protocol being used is valid by resulting in the measured respirable fraction within the claim limits of the present application and then such specific protocol testing repeated with a proposed alternative product when one wishes to determine if a proposed alternative product is within the invention or not.

Once testing above is completed and the respirable fraction is determined, the dosage per actuation actually reaching the lung is estimated by multiplying the dose per actuation delivered (by the metered dose inhaler) by the respirable fraction. In cases where this is too small for the desired dosing, one of ordinary skill adjusts concentration of the active, the actuator design, the stem block jet orifice opening diameter or combination of one or more of the above and retests the modified formulation with the modified metered dose inhaler, or the original formulation with the modified metered dose inhaler or any combination thereof as appropriate. Based on those test results, the process may be repeated or not as desired until the various parameters are optimized to give a desired delivered dose of a formulation of the cannabinoid to the lungs of the subject being treated.

EXAMPLES

The following examples exemplify, but do not limit, the present invention.

Example 1

A formulation is prepared as set forth below.

| | |
|---|---|
| CBD Acid (98% pure powder) - | 97 mg = 1.55% |
| Ethanol -- | 200 mg = 3.19% |
| HFA 134a | 5970 mg = 95.23% |
| SubTotal | 6267 mg = 99.97 |

-continued

| | |
|---|---|
| CBD | 2 mg = 0.03% |
| Total | 6269 mg = 100.00% |

The formulation is prepared as follows;
98% CBD Acid powder (99 mg) is weighed out and transferred to a suitable container and ethanol (0.2 g) added till solution is observed. The solution is transferred to an appropriate aerosol container (glass, aluminum) and a metered dose inhaler valve (100 ul) crimped on. The sample is then pressure filled with 5.97 g HFA 134a. The final product is a yellow solution. This formulation will deliver about 2.0 mg of CBD acid per actuation.

Example 2

Following the procedure in example 1 except that the particular components and amounts are selected as shown in the table below, formulations of the present invention are prepared.

| | Cannabinoids | | | Cosolvent | | Propellant | |
|---|---|---|---|---|---|---|---|
| Example | (98% CBD Acid) g | (2% THC acid | mg/100 ul | (ethanol) g | % w/w of formulation | (HFA134a) g | % w/w of formulation |
| 2a | 0.049 | 0.001 | 0.05 | 0.2 | 2.1 | 9.37 | 97.40 |
| 2b | 0.0245 | 0.005 | 0.025 | 0.366 | 4.13 | 8.48 | 95.6 |
| 2c | 0.098 | 0.002 | 0.100 | 0.410 | 4.2 | 9.25 | 94.80 |

Example 3

Following the procedure in example 1 except that the particular components and amounts are selected as shown in the table below and the starting material is a 24% CBD enriched cannabinoid extract, a formulation of the present invention is prepared:

| | Cannabinoid | | | Cosolvent | | Propellant | |
|---|---|---|---|---|---|---|---|
| Example | (75% CBD) | | | | | | |
| Procedure Followed | acid oil in g | (25% THC acid oil in g) | mg/100 ul | (ethanol) g | % w/w of formulation | (HFA134a) g | % w/w of formulation |
| 1 | 0.383 | 0.128 | 7.8 | 1.18 | 18.8 | 4.8 | 78.6 |

The formulation is prepared as follows;

Cannabinoid extract oil enriched in 75% CBD Acid and 25% THC Acid (0.5117 g of oil) is weighed out and transferred to a suitable container and ethanol (1.18 g) added. The resulting solution contained some insoluble particles which were remove by filtration. It was determined that during filtration, 23% of the weight was lost. The filtered solution is transferred to an appropriate aerosol container (glass, aluminum) and a metered dose inhaler valve (100 ul) crimped on. The sample is then pressure filled with 4.81 g HFA 134a. The final product is a yellow solution. This formulation would deliver 7.75 mg of CBD Acid/THC acid per actuation.

Example 4

A formulation is prepared as set forth below.

| | |
|---|---|
| CBD Acid (99% pure powder) - | 99 mg = 1.577% |
| Ethanol -- | 200 mg = 3.2% |
| Menthol | 5 mg = 0.079% |
| HFA 134a | 5970 mg = 95.14% |
| SubTotal | 6274 mg = 99.996 |
| CBD | 1 mg = 0.0159% |
| Total | 6275 mg = 100.01% |

Example 5

Following the procedure in example 1 except that the particular components and amounts are selected as shown in the table below, formulations of the present invention are prepared:

| | | Example | | |
|---|---|---|---|---|
| | | 5a | 5b | 5c |
| Cannabinoids | (98% CBD Acid) g | 0.0049 | 0.0245 | 0.098 |
| | (2% THC acid) g | 0.001 | 0.0005 | 0.002 |
| | g/100 ul | 0.054 | 0.025 | 0.100 |
| Terpenoid | (Menthol) g | 0.0025 | 0.00125 | 0.005 |
| | % w/w of formulation | 0.026 | 0.014 | 0.05 |
| Cosolvent | (ethanol) g | 0.2 | 0.366 | 0.410 |
| | % w/w of formulation | 2.07 | 4.12 | 4.12 |
| Propellant | (HFA134a) g | 9.37 | 8.48 | 9.25 |
| | % w/w of formulation | 97.37 | 95.58 | 94.7 |
| | Total Wt 9 g | 9.623 g | 8.872 g | 9.765 |

We claim:

1. A cannabinoid component containing formulation comprising:
   (a) said cannabinoid component comprising one or more cannabinoid active agent(s)
       (i) at least one of said one or more cannabinoid active agent(s) is not selected from the group consisting of tetrahydrocannabinol (THC), tetrahydrocannabinolic acid (THCA), cannabidiol (CBD), cannabidiolic acid (CBDA) or salts thereof and
       (ii) optionally zero or one or more cannabinoids selected from the group consisting of tetrahydrocannabinol (THC), tetrahydrocannabinolic acid (THCA), cannabidiol (CBD), cannabidiolic acid (CBDA), esters, amides, and salts thereof;
   (b) a hydrofluoroalkane (HFA) propellant; and
   (c) a co-solvent for said cannabinoid active agent, which co-solvent is ethanol; and
   (d) optionally one or more terpenoids;
   said HFA propellant being present in an amount of from 50% by weight to 99.99% by weight based on the entire formulation;
   said co-solvent, being present in an amount of from 0.1% by weight up to 40% by weight based on the entire formulation; and
   said cannabinoid active agent being present, in an amount 0.01 mg/100 ul to 20 mg/100 ul relative to the total formulation when only a single cannabinoid is present, and based on the total of the two most predominantly present cannabinoid active agents present of 0.01 mg/100 ul to 20 mg/100 ul of total formulation, when more than one cannabinoid is present
   wherein the only active agents present in said formulation are (a) cannabinoid active agents optionally (b) said optional terpenoids, and optionally (c) one or more non-cannabinoid-non-terpenoid active agents which non-cannabinoid-non-terpenoid active agents are otherwise naturally present in extracts of cannabinoid containing plant materials; and
   wherein glycerol is not present in said formulation.

2. The formulation of claim 1 wherein said cannabinoid component is, subject to the limitations on cannabinoids of claim 1, selected from:
   (A) (i) an extract of a cannabinoid containing plant material, said extract containing one or more first cannabinoid active agent(s) or
       (ii) a combination of said extract and one or more additional cannabinoid active agent(s), said additional cannabinoid active agent(s) selected from the group consisting of
           (a) partially or completely purified cannabinoid compounds,
           (b) synthetic cannabinoid compounds, and
           (c) mixtures thereof; or
       (iii) an active containing material selected from the group consisting of
           (a) an extract of a cannabinoid containing plant material, said extract containing one or more first cannabinoid active agent(s),
           (b) partially or completely purified second cannabinoid active agents,
           (c) synthetic second cannabinoid active agents, and
           (d) mixtures thereof;
   wherein said first cannabinoid active agent(s) of (A)(iii) and said second cannabinoid active agent(s) of (A)(iii) being independently selected from the group consisting of:
   (a) Formula I and/or Formula IIa
       (i) wherein R1 is —CH2(OH), —CH(OH)lower alkyl, —CHO, or —C(=O)lower alkyl, or a pharmaceutically acceptable ester of any alcoholic OHs;
       R2 and R3 are independently H, lower alkyl, or together are =CH2, or =CH-lower alkyl, or =C-(lower alkyl) (lower alkyl);
       R4 is H or lower alkyl;
       R5 and R6 are independently H or lower alkyl;
       R7-R8 are independently H, lower alkyl, —CH2OH, —CHO, —COOH, or a pharmaceutically acceptable ester or pharmaceutically acceptable amide or a pharmaceutically acceptable salt thereof;
       (ii) wherein R1 is lower alkyl, —CH2(OH), —CH(OH)lower alkyl, —CHO, —C(=O)lower alkyl, or —COOH or a pharmaceutically acceptable ester or a pharmaceutically acceptable amide or a pharmaceutically acceptable salt of said —COOH or a pharmaceutically acceptable ester of any alcoholic OHs;
       at least one of R2 and R3 are independently H, or together are =CH2, or =CH-lower alkyl, or =C-(lower alkyl) (lower alkyl);
       R4 is H or lower alkyl;
       R5 and R6 are independently H or lower alkyl;

R7-R8 are independently H, lower alkyl, —CH2OH, —CHO, —COOH, or a pharmaceutically acceptable ester or pharmaceutically acceptable amide or a pharmaceutically acceptable salt thereof;

(iii) wherein R1 is lower alkyl, —CH2(OH), —CH(OH)lower alkyl, —CHO, —C(=O)lower alkyl, or —COOH or a pharmaceutically acceptable ester or a pharmaceutically acceptable amide or a pharmaceutically acceptable salt of said —COOH or a pharmaceutically acceptable ester of any alcoholic OHs;

R2 and R3 are independently H, lower alkyl, or together are =CH2, or =CH-lower alkyl, or =C-(lower alkyl) (lower alkyl);

R4 is lower alkyl;

R5 and R6 are independently H or lower alkyl;

R7-R8 are independently H, lower alkyl, —CH2OH, —CHO, —COOH, or a pharmaceutically acceptable ester or pharmaceutically acceptable amide or a pharmaceutically acceptable salt thereof;

(iv) wherein R1 is lower alkyl, —CH2(OH), —CH(OH)lower alkyl, —CHO, —C(=O)-lower alkyl, or —COOH or a pharmaceutically acceptable ester or a pharmaceutically acceptable amide or a pharmaceutically acceptable salt of said —COOH or a pharmaceutically acceptable ester of any alcoholic OHs;

R2 and R3 are independently H, lower alkyl, or together are =CH2, or =CH-lower alkyl, or =C-(lower alkyl) (lower alkyl);

R4 is H or lower alkyl;

at least one of R5 and R6 is lower alkyl;

R7-R8 are independently H, lower alkyl, —CH2OH, —CHO, —COOH, or a pharmaceutically acceptable ester or pharmaceutically acceptable amide or a pharmaceutically acceptable salt thereof;

(v) wherein R1 is lower alkyl, —CH2(OH), —CH(OH)lower alkyl, —CHO, —C(=O)lower alkyl, or —COOH or a pharmaceutically acceptable ester or pharmaceutically acceptable amide or a pharmaceutically acceptable salt of said —COOH or a pharmaceutically acceptable ester or pharmaceutically acceptable salt of any alcoholic OHs;

R2 and R3 are independently H, lower alkyl, or together are =CH2, or =CH-lower alkyl, or =C-(lower alkyl) (lower alkyl);

R4 is H or lower alkyl;

R5 and R6 are independently H or lower alkyl;

at least one of R7-R8 is lower alkyl, —CH2OH, or —CHO, and the other of R7-R8 is lower alkyl, —CH2OH, —CHO, or —COOH, or a pharmaceutically acceptable ester or pharmaceutically acceptable amide or a pharmaceutically acceptable salt thereof; and (vi) compounds of Formula Ia wherein R1 is lower alkyl, —CH2(OH), —CH(OH)lower alkyl, —CHO, —C(=O)lower alkyl, or —COOH or a pharmaceutically acceptable ester or pharmaceutically acceptable amide or a pharmaceutically acceptable salt of said —COOH or a pharmaceutically acceptable ester of any alcoholic OHs;

R2 and R3 are independently H, lower alkyl, or together are =CH2, or =CH-lower alkyl, or =C-(lower alkyl) (lower alkyl); R4 is H or lower alkyl;

R5 and R6 are independently H or lower alkyl;

R7-R8 are independently H, lower alkyl, —CH2OH, —CHO, —COOH, or a pharmaceutically acceptable ester or pharmaceutically acceptable amide;

wherein all recitations of "alkyl" without specific carbon length or modified by "lower" being C1-C10 in length; and all recitations of "alkyl" and "lower alkyl" being understood as being straight chain or branched chain; and (b) formulae III-IX and further Formula IIb and mono-, di-, and tri-saturations at ring positions 1-6 of Formula IIb other than compounds of Formula IIa wherein R1 is lower alkyl, —CH2(OH), —CH(OH) lower alkyl, —CHO, —C(=O)— lower alkyl, or —COOH or a pharmaceutically acceptable ester or a pharmaceutically acceptable amide or a pharmaceutically acceptable salt of said —COOH or a pharmaceutically acceptable ester of any alcoholic OHs;

R2 and R3 are independently H, lower alkyl, or together are =CH2, or =CH— lower alkyl, or =C-(lower alkyl) (lower alkyl);

R4 is H or lower alkyl;

R5 and R6 are independently H or lower alkyl;

and with respect to Formula VI, R4 and R5 may together also form CH2=;

R7-R10 are independently H, lower alkyl, —CH2OH, —CHO, —COOH, or a pharmaceutically acceptable ester or pharmaceutically acceptable amide or a pharmaceutically acceptable salt thereof;

R11-R16 independently being H, or lower alkyl;

wherein all recitations of "alkyl" without specific carbon length or modified by "lower" being C1-C10 in length; and all recitations of "alkyl" and "lower alkyl" being understood as being straight chain or branched chain; and (c) tetrahydrocannabinol (THC), a tetrahydrocannabinolic acid (THC acid), cannabidiol (CBD), cannabidiolic acid (CBD acid), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, isomers thereof, and mixtures thereof; and (d) mixtures thereof;

(B) a hydrofluoroalkane (HFA) propellant; and (C) a co-solvent selected from the group consisting of ethanol;

(D) optionally one or more terpenoids;

said HFA propellant being present in an amount of from 50% by weight to 99.99% by weight based on the entire formulation;

said co-solvent, being present in an amount of from 0.1% by weight up to 40% by weight based on the entire formulation;

and said extract (A)(i) or said combination of said extract and said additional cannabinoid active agent(s) (A)ii) or said active containing material (A)(iii) being present, in an amount based on the total of the two most predominantly present cannabinoid active agents of from 0.01 mg/100 ul to 20 mg/100 ul of total formulation;

wherein said extract (A)(i) and A(ii) contains from 1 up to 5 major cannabinoid pairs, each major cannabinoid pair consisting of the acid and non-acid forms thereof, wherein to be considered a major cannabinoid pair, the cannabinoid pair must be at least 20% of the total cannabinoid content of the formulation, wherein said extract (A)(i), (A)(ii), and (A)(iii)(a) is each obtained in the absence of applying heat at all or in the absence of applying heat greater than 50° wherein Formulae I-IX are:

Formula I

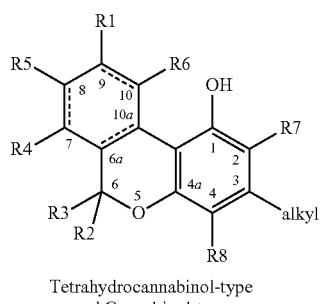

Tetrahydrocannabinol-type
and Cannabinol-type

Formula Ia

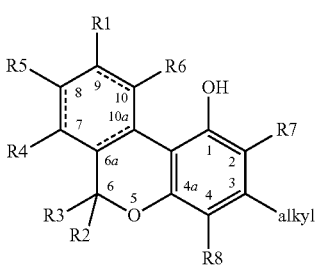

Formula II

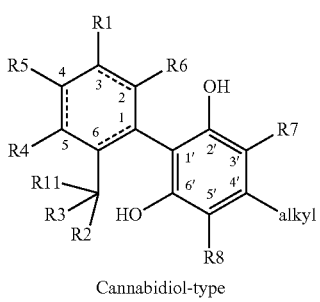

Cannabidiol-type

Formula IIa

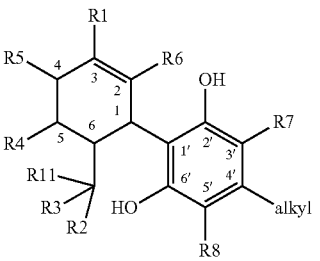

Formula IIb

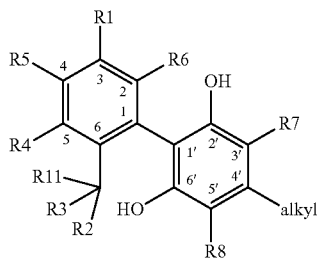

Formula III

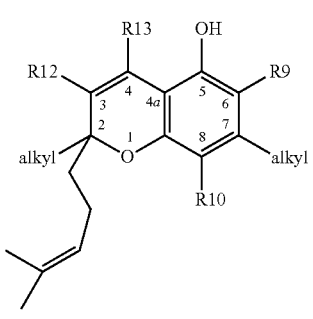

Cannabichromene-type

Formula IV

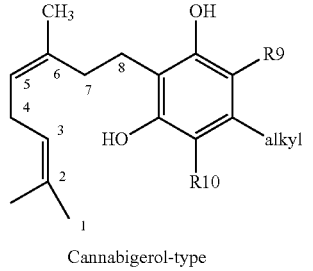

Cannabigerol-type

Formula V

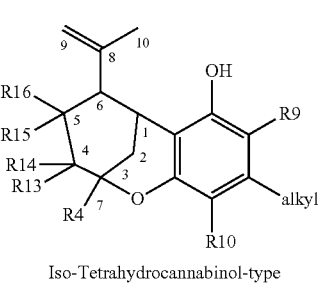

Iso-Tetrahydrocannabinol-type

Formula VI

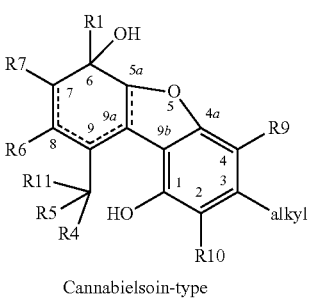

Cannabielsoin-type

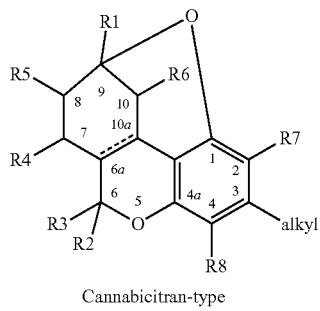

Cannabicitran-type

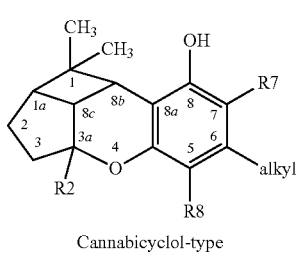

Cannabicyclol-type

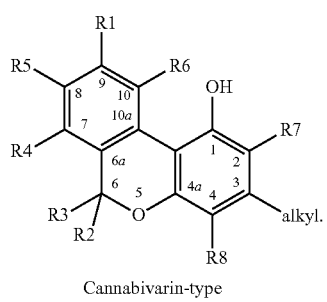

Cannabivarin-type

3. The formulation of claim 2 comprising:
a cannabinoid material comprising at least one cannabinoid active agent, said cannabinoid material being an extract of a cannabinoid containing plant material;
a hydrofluoroalkane (HFA) propellant;
a co-solvent for said cannabinoid active agent which is ethanol; and
optionally one or more terpenoids;
said HFA propellant being present in an amount of from 50% by weight to 99.99% by weight based on the entire formulation;
said co-solvent, being present in an amount of 0.1% by weight up to 21.05% by weight based on the entire formulation; and
said cannabinoid material being present, in an amount based on the total of the two most predominantly present cannabinoid active agents of 0.01 mg/100 ul to 13.3 mg/100 ul of total formulation;
wherein said extract contains from 1 up to 5 major cannabinoid pairs, each major cannabinoid pair consisting of the acid and non-acid forms thereof,
wherein to be considered a major cannabinoid pair, the cannabinoid pair must be at least 20% of the total cannabinoid content of the formulation,
said major cannabinoid pairs being present collectively in an amount greater than 80% of the cannabinoids present in said extract,
wherein each of said major cannabinoid pairs is present substantially in the acid form thereof, and
wherein said extract is obtained in the absence of applying heat at all or in the absence of applying heat greater than 50° C.

4. The formulation of claim 2 wherein component (A) is selected from (A)i) and (a)(ii).

5. The formulation of claim 2 wherein the co-solvent is present in an amount of from 0.1% by weight to 15% by weight based on the entire formulation.

6. The formulation of claim 2 wherein the propellant is selected from HFA 134a and HFA 227.

7. The formulation of claim 1 wherein said at least one cannabinoid is selected from the group consisting of cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, isomers thereof, and mixtures thereof; and
said optionally zero or one or more cannabinoids is selected from the group consisting of tetrahydrocannabinol (THC), a tetrahydrocannabinolic acid (THC acid), cannabidiol (CBD), cannabidiolic acid (CBD acid), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, isomers thereof, and mixtures thereof.

8. The formulation of claim 1, wherein cannabidiol and cannabidiolic acid are present among the top five most predominantly present cannabinoid materials in said formulation.

9. The formulation of claim 1 comprising:
a cannabinoid material comprising at least one cannabinoid active agent, said cannabinoid material, subject to the limitations of claim 1, being selected from the group consisting of (a) an extract of a cannabinoid containing plant material, such extract being a raw extract, or a partially or a highly purified form of said raw extract; (b) a synthetic cannabinoid compound in partially or highly purified form; and (c) mixtures thereof;
at least one hydrofluoroalkane (HFA) propellant;
optionally at least one co-solvent for said cannabinoid active agent selected from the group consisting of ethanol;
and optionally one or more terpenoids;
said HFA propellant(s) being present in a total amount of from 50% by weight to 99.99% by weight based on the entire formulation;
said co-solvent, being present in an amount of from 0.1% by weight up to 40% by weight based on the entire formulation; and
said cannabinoid material being present, in an amount of 0.01 mg/100 ul to 20 mg/ul of total formulation if only one cannabinoid is present and based on the total of the two most predominantly present active cannabinoid materials present of 0.01 mg/100 ul to 20 mg/100 ul of total formulation when two or more cannabinoids are present;
wherein said formulation contains from 1 up to 5 major cannabinoid pairs, each major cannabinoid pair consisting of the acid and non-acid form of said cannabinoid, said acid form and said non-acid form differing from each other in the presence in the acid form of a carboxy group or a pharmaceutically acceptable salt or ester of said carboxy group and the absence thereof in the non-acid form;

wherein each major cannabinoid pair is present in an amount of at least 20% w/w of the total cannabinoid content of the formulation and the total major cannabinoid pair content is collectively at least 80% w/w of the entire formulation cannabinoid content.

10. The formulation of claim 9 further containing one or more minor cannabinoids, each minor cannabinoid being present in an amount of not more than 20% w/w of the combined contributions of an acid and a non-acid form thereof relative to the total cannabinoid content of said formulation, and the total of all minor cannabinoids being not more than 20% w/w of the total cannabinoid content of the entire formulation.

11. The formulation of claim 1 wherein said at least one terpenoid is present.

12. The formulation of claim 9 wherein said at least one terpenoid is present.

13. The formulation of claim 12 wherein said terpenoid is selected from the group consisting of camphene, camphor, carene, caryophyllene, geraniol, humulene, limonene, linalool, menthol, myrcene, phellandrene, pinene, pulegone, sativene, terpineol, terpinolene, and mixtures thereof; and when present, is present in an amount based on the entire formulation of 0.005% w/w to 0.1% w/w.

14. The formulation of claim 11 wherein said terpenoid is selected from the group consisting of camphene, camphor, careen, caryophyllene, geraniol, humulene, limonene, linalool, menthol, myrcene, phellandrene, pinene, pulegone, sativene, terpineol, terpinolene, and mixtures thereof; and when present, is present in an amount based on the entire formulation of 0.005% w/w to 0.1% w/w.

15. The formulation of claim 9 wherein the propellant is selected from HFA 134a and HFA 227.

16. The formulation of claim 10 wherein a first cannabinoid is selected from the group consisting of cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, and isomers thereof, and mixtures thereof and optionally additional cannabinoids selected from the group consisting of a tetrahydrocannabinol (THC), a tetrahydrocannabinolic acid (THC acid), cannabidiol (CBD), cannabidiolic acid (CBD acid), cannabigerolic acid, cannabigerol, cannabigerovarinic acid, cannabigerolovarin, cannabichromenic acid, cannabichromene, cannabidivarin, cannabidivarinic acid, tetrahydrocannabivarinic acid, tetrahydrocannabivarin, cannabivarinic acid, cannabivarin, cannabinolic acid, cannabinol, and isomers thereof, and mixtures thereof.

17. The formulation of claim 13 wherein THCA and CBDA are present among the top five most predominantly present cannabinoid materials in said formulation.

18. A method of administration of a cannabinoid material while substantially avoiding first-pass metabolism thereof associated with oral administrations and avoiding heat associated chemical alteration of one or more of the active agent components of said formulation comprising administering the formulation of claim 1 via a metered dose inhalation delivery system in the absence of any heating or with heating to not more than 40° C.

19. The method of administration of claim 18 wherein said delivery system using said formulation delivers a shot weight having 0.01 mg/100 ul to 20 mg/100 ul of cannabinoid therein with a respirable fraction of at least 30% w/w relative to the cannabinoid content delivered by the shot weight.

20. A method of treating a cannabinoid responsive condition comprising delivering a cannabinoid material via the method of administration of claim 18.

21. A method of providing an effective therapeutic effect of a cannabinoid acid from a formulation containing said cannabinoid acid and optionally one or more additional cannabinoid materials comprising administering said cannabinoid acid, optionally together with said one or more other cannabinoid materials via the method of claim 18, at a lower total daily dose of the total cannabinoid content of said formulation relative to the total cannabinoid/cannabinoid acid daily dose needed to obtain the same effective therapeutic effect via each of an oral ingestion, sublingual administration, smoking, vaporizing, and topical administration of the same cannabinoid profile and same ratios amongst the cannabinboids/cannabinoid acids as in said formulation.

22. The method of claim 18 wherein said method provides said effective therapeutic amount at a lower total dose than administration via each of oral ingestion, smoking, or vaporized inhalation administration when administering a composition having the same cannabinoid and cannabinoid acid profile and same relative ratios amongst the cannabinoids and cannabinoid acids as are present in said formulation.

23. A method of treating a cannabinoid and/or cannabinoid acid responsive condition while substantially avoiding or substantially reducing psychotropic effects of cannabinoid non-acid forms due to cannabinoid acid decarboxylations comprising administering at least one cannabinoid acid compound, optionally together with another cannabinoid in a formulation of claim 1 via a metered dose inhaler system wherein said effective amount of said cannabinoid and said cannabinoid acid is substantially reduced compared to oral ingestion, smoked, vaporized inhalation delivery, or topical administration of said cannabinoid acid, alone or optionally with said additional cannabinoid respectively as are present in said formulation being delivered via said metered dose inhalation.

24. A cannabinoid component containing formulation consisting of:
  (a) said cannabinoid component consisting of one or more cannabinoid active agent(s)
    (i) at least one of said one or more cannabinoid active agent(s) is not selected from the group consisting of tetrahydrocannabinol (THC), tetrahydrocannabinolic acid (THCA), cannabidiol (CBD), cannabidiolic acid (CBDA) or salts thereof and
    (ii) optionally zero or one or more cannabinoids selected from the group consisting of tetrahydrocannabinol (THC), tetrahydrocannabinolic acid (THCA), cannabidiol (CBD), cannabidiolic acid (CBDA), esters, amides, and salts thereof;
  (b) a hydrofluoroalkane (HFA) propellant; and
  (c) a co-solvent for said cannabinoid active agent, which co-solvent is selected from the group consisting of ethanol;
  (d) optionally one or more terpenoids; and
  (e) optionally non-cannabinoid-non-terpenoid active agents and inactive agents, each of said optionally non-cannabinoid-non-terpenoid active agents and inactive agents being selected from the group consisting of those naturally found in extracts of cannabinoid containing plant materials;
  said HFA propellant being present in an amount of from 50% by weight to 99.99% by weight based on the entire formulation;

said co-solvent, being present in an amount of from 0.1% by weight up to 40% by weight based on the entire formulation; and said cannabinoid active agent being present, in an amount 0.01 mg/100 ul to 20 mg/100 ul relative to the total formulation when only a single cannabinoid is present, and based on the total of the two most predominantly present cannabinoid active agents present of 0.01 mg/100 ul to 20 mg/100 ul of total formulation, when more than one cannabinoid is present wherein glycerol is not present in said formulation.

* * * * *

UNITED STATES PATENT AND TRADEMARK OFFICE
CERTIFICATE OF CORRECTION

PATENT NO. : 10,588,870 B2  
APPLICATION NO. : 16/044802  
DATED : March 17, 2020  
INVENTOR(S) : Eck et al.

Page 1 of 7

It is certified that error appears in the above-identified patent and that said Letters Patent is hereby corrected as shown below:

In the Specification

Column 4, Lines 40-54, the currently printed structure designated Formula 1:

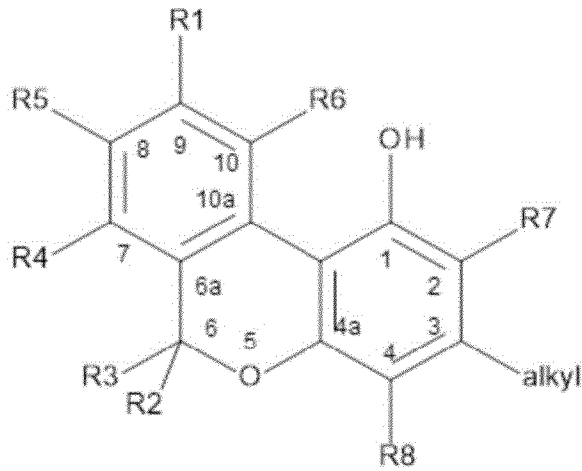

Should be replaced with:

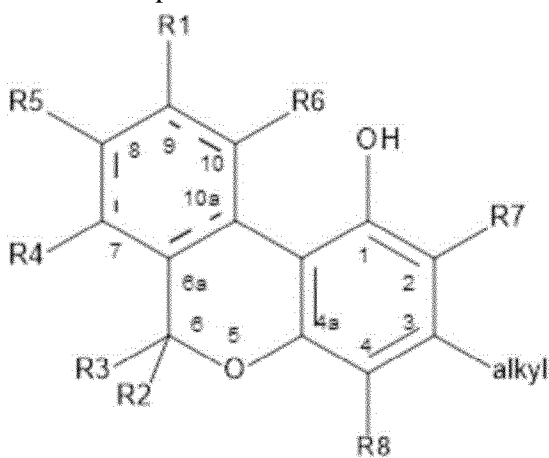

Signed and Sealed this  
Thirtieth Day of June, 2020

Andrei Iancu  
*Director of the United States Patent and Trademark Office*

CERTIFICATE OF CORRECTION (continued)
U.S. Pat. No. 10,588,870 B2

Page 2 of 7

Column 4, between Lines 57 and 58, after "cannabinol-type" and before the structure shown in Column 4, Lines 58-66. Insert --Formula Ia--

Column 5, Lines 2-12, the currently printed structure designated Formula II:

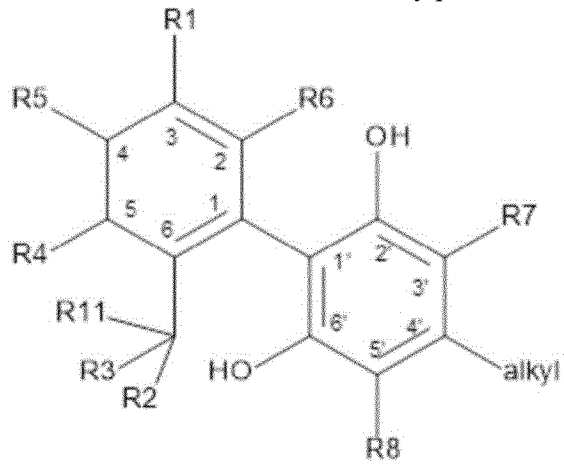

Should be replaced with:

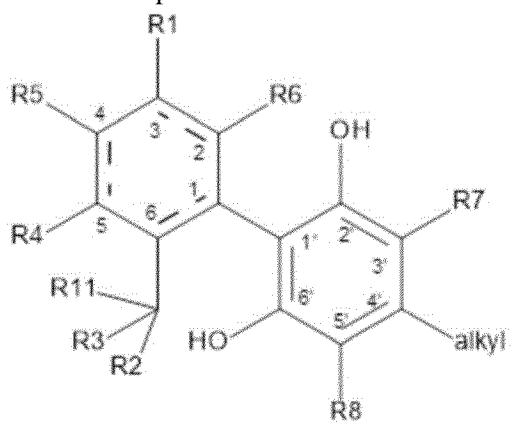

Column 6, Lines 41-50, the currently printed structure designated Formula VI:

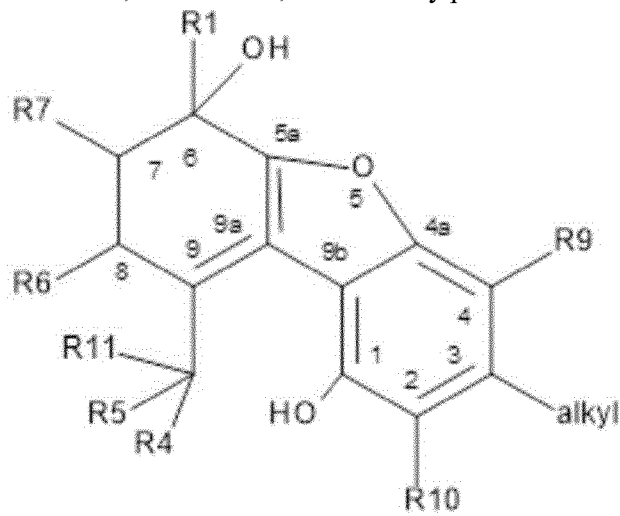

CERTIFICATE OF CORRECTION (continued)
U.S. Pat. No. 10,588,870 B2

Should be replaced with:

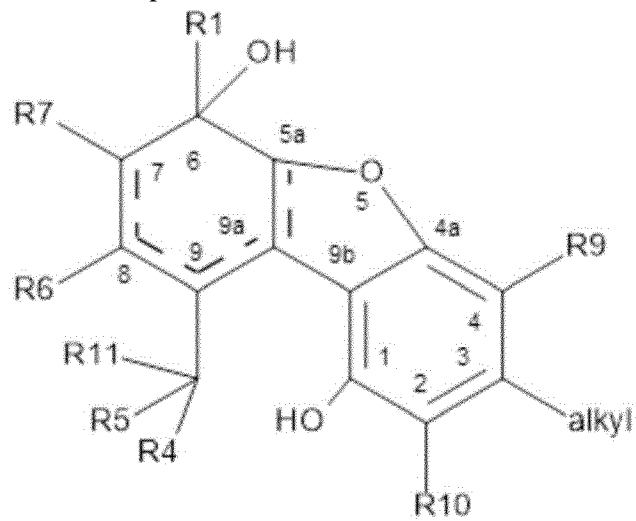

Column 6, Lines 56-65, the currently printed structure designated Formula VII:

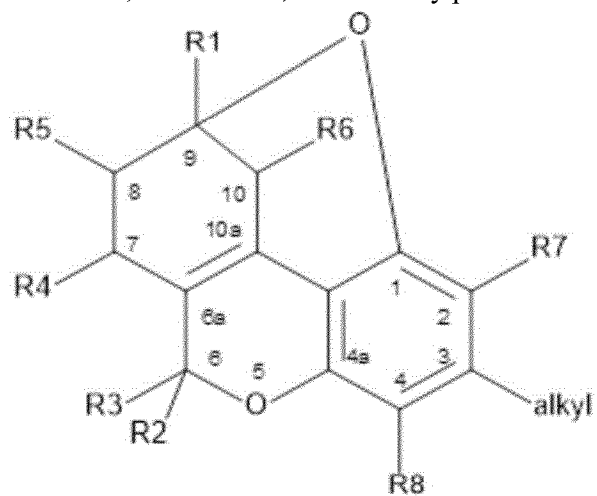

Should be replaced with:

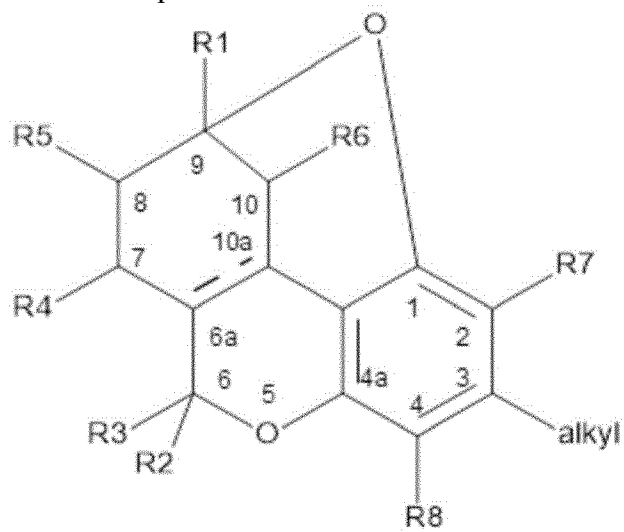

Column 7, Lines 2-10, the currently printed structure designated Formula VIII:

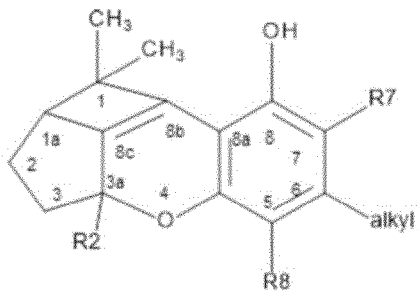

Should be replaced with:

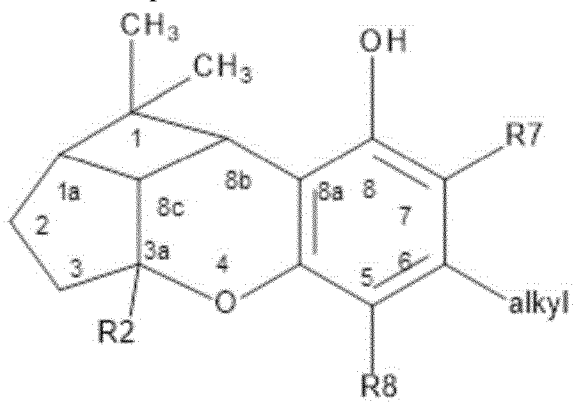

In the Claims

Column 17, Claim 1, Line 60, change "99.99% by weight" to "99.5% by weight"

Column 17, Claim 1, Lines 62-64, change "0.1% by weight up to 40% by weight based on the entire formulation" to "0.2% by weight up to 30% by weight based on the total of said propellant and said co-solvent"

Column 19, Claim 2, Lines 45-46, delete "or pharmaceutically acceptable salt"

Column 20, Claim 2, Line 59, change "99.99% by weight" to "99.5% by weight"

Column 20, Claim 2, Lines 61-63, change "0.1% by weight up to 40% by weight based on the entire formulation" to "0.2% by weight up to 30% by weight based on the total of said propellant and said co-solvent"

CERTIFICATE OF CORRECTION (continued)
U.S. Pat. No. 10,588,870 B2

Column 21, Claim 2, the currently printed structure designated as Formula Ia:

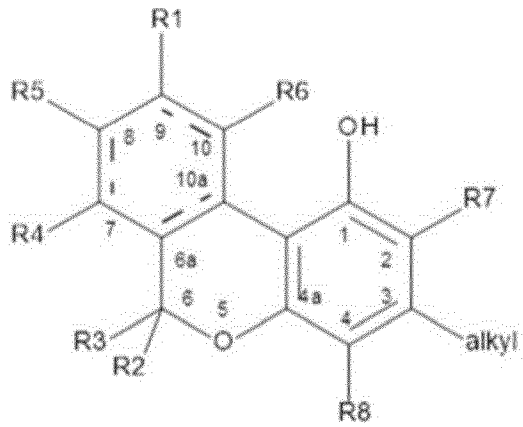

Should be replaced with:

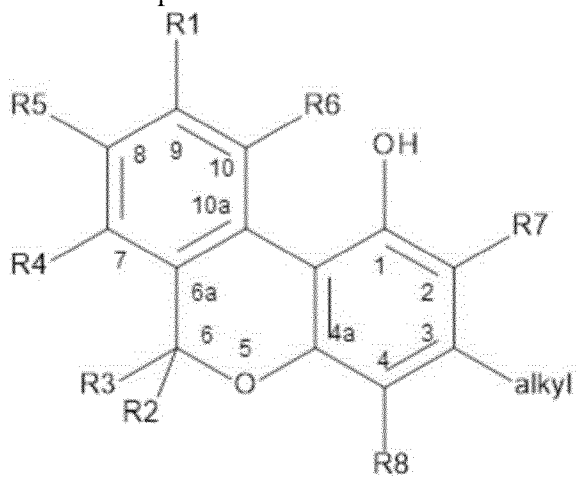

Column 22, Claim 2, the currently printed structure designated as Formula III:

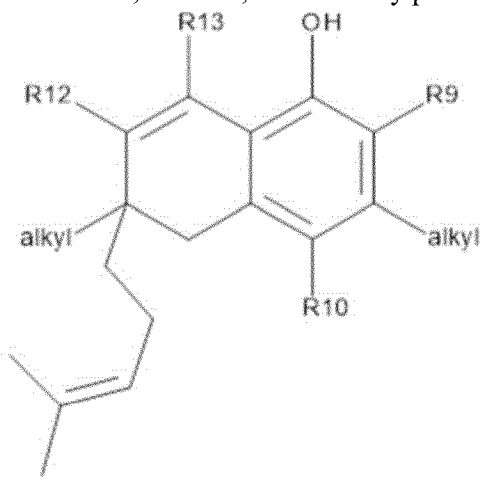

Should be replaced with:
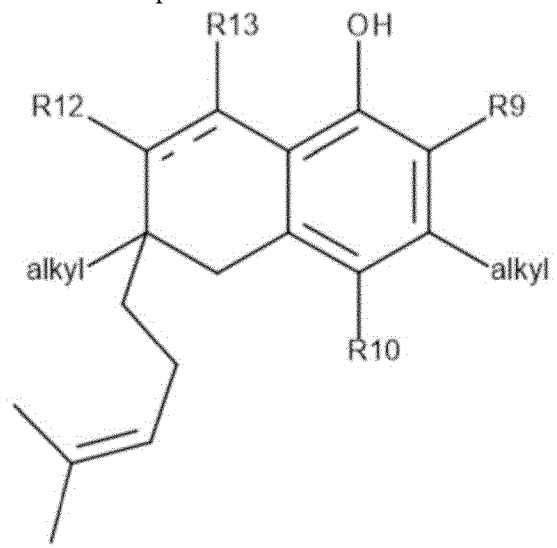
Column 22, Claim 2, the currently printed structure designated as Formula IV:
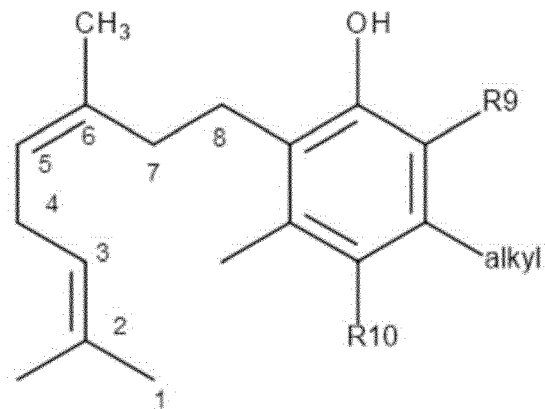
Should be replaced with:
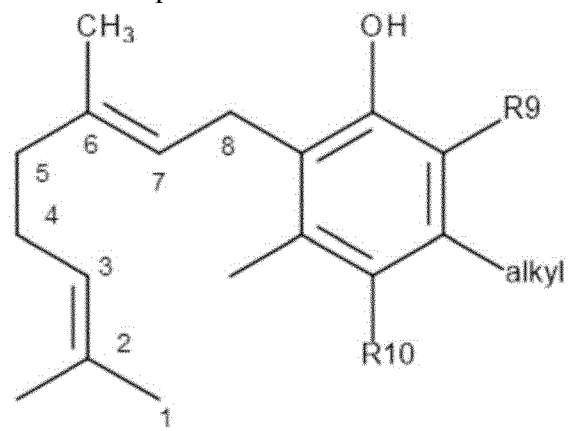
Column 23, Claim 3, Line 46, change "99.99% by weight" to "99.5% by weight"

CERTIFICATE OF CORRECTION (continued)
U.S. Pat. No. 10,588,870 B2

Column 23, Claim 3, Lines 48-50, change "0.1% by weight up to 21.05% by weight based on the entire formulation" to "0.2% by weight up to 25% by weight based on the total of said propellant and said co-solvent"

Column 23, Claim 3, Lines 58-59, change "0.01 mg/100 ul to 13.3 mg/100 ul" to "0.01 mg/100 ul to 15 mg/100 ul"

Column 24, Claim 5, Lines 4-5, change "0.1% by weight to 15% by weight based on the entire formulation" to "0.2% by weight to 15% by weight based on the total of said propellant and said co-solvent"

Column 24, Claim 9, Line 47, change "99.99% by weight" to "99.5% by weight"

Column 24, Claim 9, Lines 49-51, change "0.1% by weight up to 40% by weight based on the entire formulation" to "0.2% by weight up to 30% by weight based on the total of said propellant and said co-solvent"

Column 26, Claim 24, Line 66, change "99.99% by weight" to "99.5% by weight"

Column 27, Claim 24, Lines 1-2, change "0.1% by weight up to 40% by weight based on the entire formulation" to "0.2% by weight up to 30% by weight based on the total of said propellant and said co-solvent"